US00PP36679P3

(12) United States Plant Patent
Hansen

(10) Patent No.: US PP36,679 P3
(45) Date of Patent: May 13, 2025

(54) ***BERGENIA* PLANT NAMED 'Happily Ever After'**

(50) Latin Name: ***Bergenia* hybrid**
Varietal Denomination: Happily Ever After

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 176 days.

(21) Appl. No.: 18/445,327

(22) Filed: Jul. 11, 2023

(65) Prior Publication Data

US 2025/0024766 P1 Jan. 16, 2025

(51) Int. Cl.
*A01H 5/02* (2018.01)
*A01H 6/80* (2018.01)

(52) U.S. Cl.
USPC ..... Plt./409
CPC ..... *A01H 6/80* (2018.05); *A01H 5/02* (2013.01)

(58) Field of Classification Search
USPC ..... Plt./409
CPC ..... A01H 5/02
See application file for complete search history.

*Primary Examiner* — Kent L Bell

(57) ABSTRACT

A new and distinct Heartleaf *Bergenia* plant, *Bergenia* plant named 'Happily Ever After' with a dense mounded habit, medium-sized, densely-arranged, deep-green, glossy, ovate, evergreen foliage, and large, white becoming lightly blushed with pink, campanulate flowers on tall upright panicles over a long period beginning in spring. The flowers hold up well in the garden as a landscape plant or as cut flowers. The foliage develops a reddish blush on the front and deeper red on the back with cool fall temperatures. The new plant has a medium growth rate and the foliage is naturally resistant to deer and rabbit foraging.

1 Drawing Sheet

Botanical designation: *Bergenia* hybrid.
Cultivar denomination: 'Happily Ever After'.

STATEMENT REGARDING PRIOR DISCLOSURES UNDER 37 CFR 1.77(B)(6)

The first non-enabling disclosure of the claimed plant was Feb. 1, 2023, when the claimed plant was displayed as a photograph with a non-enabling brief description on a website maintained by Walters Gardens, Inc., who obtained the plant and all information relating thereto, from the inventor. The first plants sold of *Bergenia* 'Happily Ever After' were by Walters Gardens, Inc. on Jul. 10, 2023, from the first offer for sale on Aug. 19, 2022. Walters Gardens, Inc. obtained the new plant and all information about the new plant directly from the inventor. No other plants have been sold earlier than this date anywhere in the world, nor has any disclosure of the new plant been made more than one year prior to the filing date of this application, and such disclosure within one year was either derived directly or indirectly from the inventor.

BACKGROUND OF THE PLANT

The present invention relates to the new and distinct Heartleaf *Bergenia* herein also referred to as *Bergenia* 'Happily Ever After', by the cultivar name, 'Happily Ever After', or as the new plant. The new plant was hybridized by the inventor on Apr. 23, 2014, from a cross-pollination plant of *Bergenia* 'Angle Kiss' (not patented) as the female or seed parent and the unreleased, unnamed, proprietary hybrid known only as Dec. 1, 2018 (not patented) as the male or pollen parent. The cross was performed in a greenhouse of a wholesale perennial grower in Zeeland, Michigan. The single seedling represented by 'Happily Ever After' was selected from a group of seedlings by the inventor, isolated, compared in subsequent years to other *Bergenia* and subsequently found to be different from all cultivars known to the discoverer, and given the breeder code 14-2-2 through the remaining evaluation process.

Asexual propagation at the same nursery in Zeeland, MI, USA initially by basal cuttings and later by shoot tip sterile tissue culture has shown 'Happily Ever After' to be stable and reproduce true to type in successive generations since late summer of 2016.

SUMMARY OF THE PLANT

*Bergenia* 'Happily Ever After' has not been observed in all possible environmental conditions. The phenotype may vary slightly with changes in environments such as light intensity, fertility, water availability, etc. without, however any variation in genotype.

*Bergenia* 'Happily Ever After' is distinct from all cultivars known to the inventor in the following traits:

1. Dense mounded habit;
2. Medium-sized, densely-arranged, deep-green, glossy, obovate, evergreen foliage;
3. Foliage develops reddish blush on the front and deeper red on the back with cool fall temperatures.
4. Leaf margins are finely serrulate and ciliolate;
5. Branched, upright panicles of large, campanulate white flowers becoming lightly blushed with pink over a long period in spring;
6. Medium growth rate;
7. The foliage is naturally resistant to deer and rabbit.

The cultivar *Bergenia* 'Happily Ever After' is most similar to: 'Apple Blossom' U.S. Plant Pat. No. 15,101, 'Beethoven' (not patented) U.S. Plant Pat. No. 7,344, 'Biedermeier' (not patented), 'Bressingham White' (not patented), and 'Frau Holle' (not patented).

'Apple Blossom' has a smaller habit, smaller foliage, and smaller inflorescences with darker purplish-pink flowers. 'Beethoven' is a cross between a selection of *B. stracheyi* and *crassifolia* and has a smaller habit, pinkish-white flowers, on smaller inflorescences, and the foliage has a less serrulate or dentate margin. 'Biedermeier' has a smaller habit, lighter green foliage, and the flowers are light pink and flatter and less imbricate. 'Bressingham White' has a smaller and flatter habit with smaller inflorescences of white. 'Frau Holle' has a larger habit and lightly blushed pink flowers, and the foliage is more chartreuse with reddish tinting along the margins. None of the above comparison plants have a ciliolate margin.

The female parent, 'Angel Kiss', has a smaller habit with shorter, smaller peduncles, much smaller foliage, and the leaf margin is not ciliolate. The male parent has smaller white flowers at least one week earlier, and the foliage is more deciduous with a more ciliolate margin.

BRIEF DESCRIPTION OF THE DRAWINGS

The color drawings illustrate the overall characteristics of *Bergenia* 'Happily Ever After' as a two-year-old plant. The colors are as true as reasonably possible given the technology available. The color values may vary slightly depending on light intensity and quality.

DETAILED BOTANICAL DESCRIPTION

Figure 1:
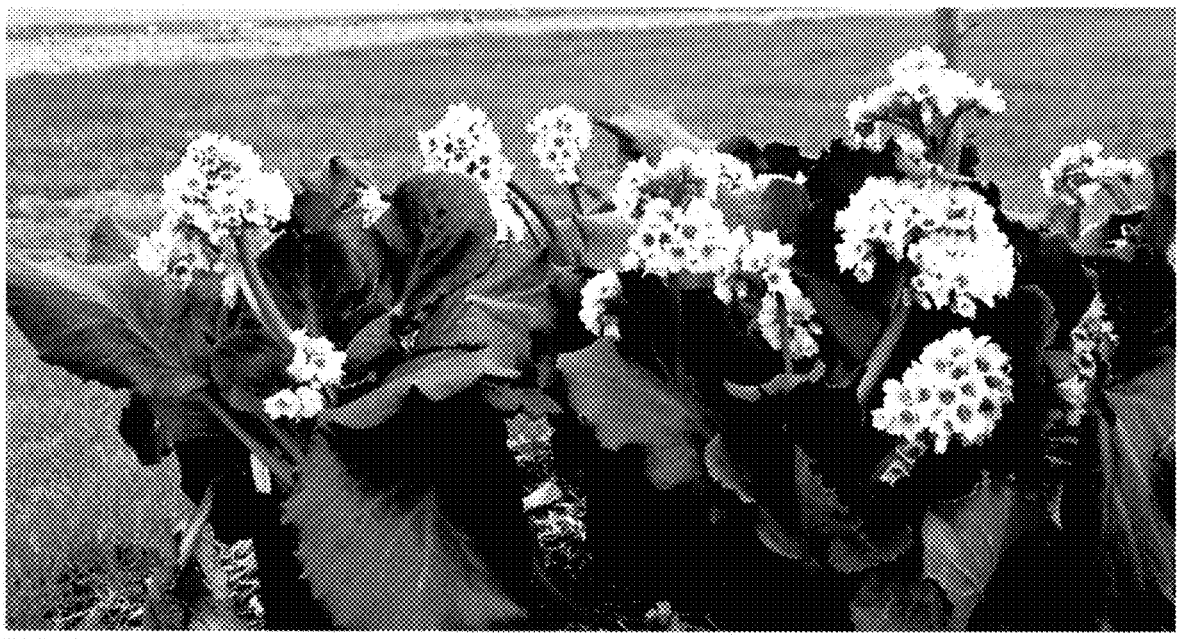
FIG. 1 shows the new plant in containers with foliage and flowers.
Figure 2:
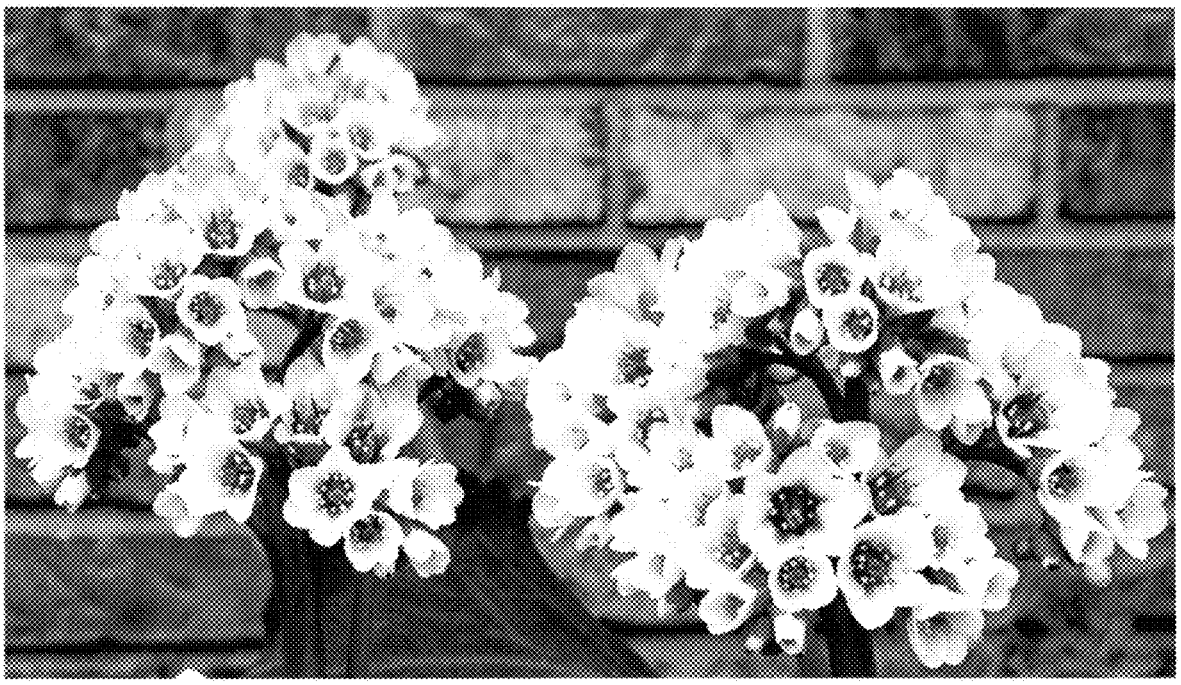
FIG. 2 shows a close-up of the panicles of the new plant.

The following description is based on two-year-old plants growing in a partially-shaded greenhouse and in an outdoor shaded trial garden in Zeeland, MI, USA. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent 'Angel Kiss'; male or pollen parent 12-1-8;

Asexual propagation: Division of tissue culture plants, about 21 days to initiate roots; time to finish 25 mm plugs in a one-gallon container about 3 months; moderate growth rate;

Plant habit: Upright, spreading, herbaceous, evergreen, winter-hardy, perennial mound; with heavily branched flower stems; with about 6 shoots per plant; shoots to about 7 cm long and about 3.5 cm diameter;

Plant size: Foliage up to about 55 cm wide and about 48 cm tall; flowering to about 60 cm wide and about 72 cm tall;

Leaves: Alternate; simple; coriaceous; obovate to ovate; adaxial and abaxial surface lustrous; rounded apex; cuneate base; margin finely crenate and ciliolate; to 32 cm long and 23 cm wide, average about 24 cm long and about 17 cm wide;

Leaf color: Young expanding leaves adaxial nearest blend of RHS 137B and RHS 146A and abaxial between RHS 146C and RHS 146B; mature leaves adaxial between RHS 139A and RHS NN137A, abaxial between RHS 143A and RHS 138A; winter color developing variable, moderate to strong blush of nearest RHS 187A adaxial and nearest RHS 187B abaxial;

Veins: Pinnate;

Vein color: Adaxial nearest RHS 137A, abaxial between RHS 146D and RHS 145A;

Inflorescence: Branched panicle; about 7 per plant; to about 72 cm long and 16 mm diameter at base, flowering portion to about 25 cm tall and 16.5 cm wide; cylindrical; lustrous; glabrous; aspect upright;

Peduncle color: Variable, proximal portion nearest blend of RHS 145C and RHS 146D, distally nearest RHS 146D with minor to blushing to nearly solid nearest RHS 178B;

Branches: Cylindrical; glabrous; lustrous; ascending upwardly to about 80° above horizontal; to about 26 cm long and 6 mm diameter; with branchlets to about 12 cm long and 3 mm diameter;

Branch and branchlet color: Proximal portion nearest blend of RHS 145C and RHS 146D, distally nearest RHS 146D with minor to blushing to nearly solid nearest RHS 178B;

Flower: Single; perfect; campanulate; on terminal branches; about 30 mm across, about 24 mm long; attitude outwardly to slightly drooping;

Flower fragrance: None detected;

Calyx: Campanulate; to about 12 mm wide and 20 mm long;

Sepals: Typically, five, rarely six or seven; ovate; broadly acute apex; truncate base; margin entire; glabrous and lustrous adaxial, and abaxial lustrous and sparsely glandular; about 12 mm long and about 7 mm wide;

Sepal color: Variable; adaxial nearest RHS 146C with thin marginal rim nearest RHS 178B; abaxial distally nearest RHS 146C with light to heavy blush nearest RHS 178B to nearly solid base nearest RHS 178B;

Flowering period: Beginning early spring, for about 4 weeks; producing up to 14 flowers per branch and up to 60 flowers per panicle;

Individual flower longevity: 7 to 10 days as cut flower or in the landscape;

Flower buds one day prior to opening: Oblong, acute apex, rounded base; about 19 mm long and 7 mm diameter;

Flower bud color one day prior to opening: Exposed petals nearest RHS NN155D, sepals nearest RHS 146C with a marginal rim of nearest RHS 178B;

Pedicel: Cylindrical; glaucous; lustrous; sparsely glandular; to about 13 mm long and 2.5 mm diameter; average about 5 mm long and 2.2 mm diameter;

Pedicel color: Variable; from nearest RHS 146C with blush of nearest RHS 180C to nearly solid RHS 180C;

Petals: Typically, five in a single whorl, rarely six; obovate; rounded apex; attenuate to cuneate base; margin entire; glabrous adaxial and abaxial; imbricate from near longitudinal middle to base; to about 27 mm long, 15 mm wide near middle, and 2 mm wide at base;

Petal color: Variable; adaxial nearest RHS NN155D when initially open, developing a faint blush of nearest RHS 59C along longitudinal center and base a moderate blush of nearest RHS 59C; abaxial nearest RHS NN155D with proximal longitudinal center having a faint blush of nearest RHS 59C with maturity;

Androecium: Typically, ten; to about 16 mm long;

*Filament*.—Cylindrical to slightly applanate proximally; lustrous; glabrous; to about 15 mm long and 1 mm diameter; color variable, translucent and nearest RHS 155B to nearest RHS 180C.

*Anther*.—Ellipsoidal; basifixed; longitudinal; about 3 mm long and 2 mm across; color nearest RHS 59D.

*Pollen*.—Abundant; color nearest RHS 16D.

Gynoecium: Double; to about 16 mm long;

*Ovary*.—Partly inferior; about 5 mm across at base and 3 mm tall; color nearest RHS 160D with faint blush nearest RHS N170D.

*Style*.—Cylindrical; about 8 mm long and 4.5 mm diameter above ovary tapered to stigma; color nearest RHS 160D with faint blush nearest RHS N170D to nearest RHS N170D with maturity.

*Stigma*.—Loosely lobed; about 4 mm wide, 2 mm tall; color nearest initially between RHS 146D and RHS N170C, at flower maturity nearest RHS 148B.

Seed: Ellipsoidal; acute apex and rounded base; surface glabrous; about 2 mm long and 0.5 mm across center; color nearest RHS 200B;

*Bergenia* 'Happily Ever After' is tolerant of winter temperatures from USDA hardiness at least from zones 4 to 8. The new plant grows best with good drainage and adequate moisture. It is not known to be tolerant of diseases and pests that are common to other Heartleaf *Bergenia* cultivars.

I claim:

1. A new and distinct cultivar of *Bergenia* plant named 'Happily Ever After' as herein described and illustrated.

* * * * *